(12) United States Patent
Paris Carrizo et al.

(10) Patent No.: US 10,875,780 B2
(45) Date of Patent: Dec. 29, 2020

(54) SYNTHESIS OF NANOCRYSTALLINE BETA ZEOLITE, SYNTHESIS METHOD AND USE THEREOF IN CATALYTIC APPLICATIONS

(71) Applicants: Universitat Politecnica de Valencia, Valencia (ES); Consejo Superior de Investigaciones Cientificas (CSIC), Madrid (ES)

(72) Inventors: Cecilia Gertrudis Paris Carrizo, Valencia (ES); Eva Maria Gallego Sanchez, Valencia (ES); Maria del Rocio Diaz Rey, Valencia (ES); Marta Evelia Martinez Armero, Valencia (ES); Maria Cristina Martinez Sanchez, Valencia (ES); Manuel Moliner Marin, Valencia (ES); Avelino Corma Canos, Valencia (ES)

(73) Assignees: UNIVERSITAT POLITECNICA DE VALENCIA, Valencia (ES); CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 0 days.

(21) Appl. No.: 16/619,022

(22) PCT Filed: Jun. 5, 2018

(86) PCT No.: PCT/ES2018/070405
§ 371 (c)(1),
(2) Date: Mar. 20, 2020

(87) PCT Pub. No.: WO2018/224714
PCT Pub. Date: Dec. 13, 2018

(65) Prior Publication Data
US 2020/0216326 A1  Jul. 9, 2020

(30) Foreign Application Priority Data

Jun. 5, 2017 (ES) .................................. 201730769

(51) Int. Cl.
C01B 39/48 (2006.01)
B01J 29/70 (2006.01)
C01B 39/02 (2006.01)

(52) U.S. Cl.
CPC .......... C01B 39/48 (2013.01); B01J 29/7007 (2013.01); C01B 39/026 (2013.01);
(Continued)

(58) Field of Classification Search
CPC ... C01B 39/48; C01P 2002/60; B01J 29/7007; C07C 2529/70; B01D 2255/502
See application file for complete search history.

(56) References Cited

U.S. PATENT DOCUMENTS 3,308,069 A   3/1967  Wadlinger et al.
5,106,801 A * 4/1992  Zones .................... B01J 29/035
                                                          502/64
(Continued)

FOREIGN PATENT DOCUMENTS

EP  0659685 A1  6/1995
FR  2936791 A1  4/2010
WO  9100777    1/1991

OTHER PUBLICATIONS

Eva M. Gallego, "Simple Organic Structure Directing Agents for Synthesizing Nanocrystalline Zeolites", Article, Oct. 5, 2017, 8138-8149, vol. 8, Chemical Science, Royal Society of Chemistry.
(Continued)

Primary Examiner — David M Brunsman
(74) Attorney, Agent, or Firm — Hayes Soloway PC

(57) ABSTRACT

The present invention relates to a new process for synthesising a crystalline material comprising structure Beta zeo-
(Continued)

lite in nanocrystalline form, and which can comprise at least the following steps: (i) preparing a mixture comprising at least one source of water, at least one source of a tetravalent element Y, at least one source of a trivalent element X, at least one source of an alkali cation or alkaline earth metal cation (A), and at least one organic molecule selected from a monocyclic quaternary ammonium $R_1R_2CycloN^+$, and a quaternary ammonium substituted with a cycloalkyl group $R_3R_4R_5R_6N^+$. The molar composition of the mixture is: n $X_2O_3$:$YO_2$:a A:m OSDA1:z $H_2O$; ii) crystallising the mixture; and iii) recovering the crystalline material.

26 Claims, 3 Drawing Sheets

(52) U.S. Cl.
CPC .... *B01D 2255/502* (2013.01); *C01P 2002/01* (2013.01); *C01P 2002/60* (2013.01); *C01P 2002/72* (2013.01); *C01P 2004/03* (2013.01); *C01P 2004/64* (2013.01); *C07C 2529/70* (2013.01)

(56) References Cited

U.S. PATENT DOCUMENTS

| | | | | |
|---|---|---|---|---|
| 6,616,911 | B2* | 9/2003 | Elomari | B01D 53/86 423/706 |
| 9,158,190 | B2* | 10/2015 | Chen | G03F 7/70275 |
| 2003/0091504 | A1* | 5/2003 | Pasquale | C01B 37/005 423/706 |
| 2004/0234449 | A1* | 11/2004 | Pasquale | C07B 41/06 423/707 |

OTHER PUBLICATIONS

Zheng-Bao Yu, "Intergrown New Zeolite Beta Polymorphs with Interconnected 12-Ring Channels Solved by Combining Electron Crystallography and Single-Crystal X-Ray Diffraction", Article, Sep. 14, 2012, 3701-3706, vol. 24, Chemistry of Materials, ACS Publications.

Mingquan Tong, "Synthesis of Chiral Polymorph A-enriched Zeolite Beta with an Extremely Concentrated Fluoride Route", Article, Jun. 22, 2015, 1-10, Scientific Reports, Nature.com.

M.M.J. Treacy, "Two New Three-Dimensional Twelve-Ring Zeolite Frameworks of Which Zeolite Beta is a Disordered Intergrowth", Mar. 1988, 249-251, vol. 332, Letters to Nature, Nature.

J.E. Hazm, "Synthesis and Characterization of Gallium-Beta Zeolite from Fluoride-Containing Media", 2001, 11-25, vol. 43, Microporous and Mesoporous Materials, Elsevier.

Avelino Corma, "Sn-Zeolite Beta as a Heterogeneous Chemoselective Catalyst for Baeyer-Villiger Oxidations", Jul. 26, 2001, 423-425, vol. 412, Letters to Nature, Nature.

Haoquan Zheng, "Nanosized Inorganic Porous Materials: Fabrication, Modification and Application", Journal, 2016, 16756-16770, vol. 4 Journal of Materials Chemistry A, Royal Society of Chemistry.

M.A. Camblor, "Characterization of Nanocrystalline Zeolite Beta", 1998, 59-74, vol. 25, Microporous and Mesoporous Materials, Elsevier.

S. Mintova, "Variation of the Si/Al Ratio in Nanosized Zeolite Beta Crystals", 2006, 237-245, vol. 90, Microporous and Mesoporous Materials, Elsevier.

B. J. Schoeman, "The Synthesis of Discrete Colloidal Crystals of Zeolite Beta and their Application in the Preparation of Thin Microporous Films", Journal, 2001, 13-22, vol. 8, Journal of Porous Materials, Kluwer Academic Publishers.

G. Majano, "Zeolite Beta Nanosized Assemblies", 2005, 227-235, vol. 80, Microporous and Mesoporous Materials, Elsevier.

Olivier Larlus, "A Powerful Structure-Directing Agent for the Synthesis of Nanosized Al- and High-Silica Zeolite Beta in Alkaline Medium", 2011, 17-25, vol. 142, Microporous and Mesoporous Materials, Elsevier.

Minkee Choi, "The Synthesis of a Hierarchically Porous BEA Zeolite via Pseudomorphic Crystallization", Journal 2009, 2845-2847, Chemical Communication, The Royal Society of Chemistry.

Jie Zhu, "Highly Mesoporous Single-Crystalline Zeolite Beta Synthesized Using a Nonsurfactant Cationic Polymer as a Dual-Function Template", Journal, 2014, 2503-2510, vol. 136, Journal of the American Chemical Society, ACS Publications.

Raquel Martinez-Franco, "High-Silica Nanocrystalline Beta Zeolites: Efficient Synthesis and Catalytic 4pplic.ation", 2016, 102-108, vol. 7, Chemical Science, Royal Society of Chemistry.

\* cited by examiner

SYNTHESIS OF NANOCRYSTALLINE BETA ZEOLITE, SYNTHESIS METHOD AND USE THEREOF IN CATALYTIC APPLICATIONS

CROSS-REFERENCE TO RELATED APPLICATIONS AND PRIORITY

This patent application claims priority under section 371 from PCT Patent Application No. PCT/ES2018/070405 filed Jun. 5, 2018, which claims priority from Spanish Patent Application No. ESP201730769 filed Jun. 5, 2017. Each of these patent applications are herein incorporated by reference in its/their entirety.

The present invention relates to a new synthesis method for synthesising zeolite with crystalline structure Beta in nanocrystalline form, and to the use as a catalyst of the synthesised zeolite material according to the present synthesis method.

BACKGROUND OF THE INVENTION

The synthesis of Beta zeolite was described for the first time in aluminosilicate form using the organic molecule tetraethylammonium (TEA) as an organic structure-directing agent (OSDA) (Wadlinger et al., U.S. Pat. No. 3,308, 069, 1967). Structure Beta has a tridirectional system of interconnected channels, bound by 12-atoms, and the pore opening of which is ~6-8.5 Å (Treacy et al., Nature, 1988, 332, 249).

The use of the TEA cation as an OSDA also allows preparing the Beta zeolite with other chemical compositions, such as for example in the form of gallosilicate (Hazm et al., *Micropor. Mesopor. Mater.*, 2001, 43, 11), borosilicate (Zones et al., WO9100777, 1991), titanosilicate (Saxton et al., Eur. Pat. 0,659,685, 1994), or tinsilicate (Corma et al., *Nature*, 2001, 412, 423), among others. The possibility of preparing structure Beta zeolite with various compositions confers to it interesting catalytic properties in a large number of chemical processes, including both petrochemical and fine chemical processes.

The synthesis of zeolites in nanocrystalline form, i.e. with very small crystal sizes (<100 nm), is highly desirable, given that materials of this type allow improving the efficiency of catalytic processes requiring the presence of bulky products and/or reagents, considerably favouring their diffusion through the crystals, and minimising deactivation processes (Zheng et al. *J. Mater. Chem. A*, 2016, 4, 16756). Nevertheless, preparing a given zeolite in nanocrystalline form in an efficient and general manner, i.e. with wide chemical composition ranges, such as for example wide ranges of Si/Al, good synthesis yields (>80%), and with homogeneous particle sizes with an average particle size less than 50 nm, is a complicated task.

The first synthesis of nanocrystalline beta zeolite with crystal sizes comprised between 10 and 100 nm was prepared using TEA as OSDA in the absence of alkali cations (Camblor et al., *Micropor. Mesopor. Mater.*, 1998, 25, 59). This methodology allows the synthesis of the nanocrystalline Beta zeolite with different Si/Al ratios (from 6 to 50), but with low synthesis yields (50%) for those samples prepared with Si/Al ratios greater than 10 (Camblor et al., *Micropor. Mesopor. Mater.*, 1998, 25, 59). Other authors have described similar results using TEA as OSDA and comparable synthesis conditions (Mintova et al., *Micropor. Mesopor. Mater.*, 2006, 90, 237; Schoeman et al., *J. Porous. Mater.*, 2001, 8, 13).

The synthesis of mesoporous Beta zeolite formed by the assembly of nanocrystals comprised between 20 and 100 nm has been achieved with several Si/Al ratios and high synthesis yields (~80-90%) using TEA as OSDA through the dry gel methodology, which consists of contacting the dry solid containing all the components needed for carrying out the synthesis of zeolite with water vapour and/or volatile amine vapours at autogenous pressure and temperatures between 160 and 200° C. (Majano et al., *Micropor. Mesopor. Mater.*, 2005, 80, 227). Nevertheless, synthesis methodologies based on dry gel are more difficult to scale, introducing significant operating and economic limitations for preparing Beta zeolite in nanocrystalline form on an industrial scale.

Nanocrystalline Beta zeolite has also been synthesised with high yields through conventional hydrothermal synthesis methods, but this requires the use of bulky organic compounds, such as 4,4'-trimethylenebis(N-methyl,N-benzyl-piperidinium) (Larlus et al., *Micropor. Mesopor. Mater.*, 2011, 142, 17), 3,10-Diazoniumbicyclo[10.2.2]hexadeca-12,14,15-triene-3,3,10,10-tetramethyl dichloride (Choi et al., *Chem. Commun.*, 2009, 2845), or cationic polymers, such as polydiallyldimethylammonium (Zhu et al., *J. Am. Chem. Soc.*, 2014, 136, 2503). These synthesis methods with bulky OSDAs usually have long aliphatic chains and/or usually require the use of a number of synthesis steps, which may increase the cost of preparing the OSDA for synthesis of structure Beta in nanocrystalline form.

Recently, the synthesis of nanocrystalline Beta with crystal sizes comprised between 10-30 nm has been described with high synthesis yields, using for the preparation thereof bulky dicationic OSDAs derived from alkylpyrrolidines and alkylazepanes (Martinez-Franco et al., *Chem. Sci.*, 2016, 7, 102). The preparation of said dicationic organic molecules requires different synthesis steps which may considerably increase the cost associated with preparing the organic molecule that will be used as OSDA in the synthesis of nanocrystalline Beta zeolite. For example, the OSDAs described in (Martinez-Franco et al., *Chem. Sci.*, 2016, 7, 102), require the presence of linear dihaloalkanes, such as 1,5-dibromopentane, for example, which are used as flexibility precursors in the described dicationic OSDAs, and as a bridge between the ammonium groups. Nevertheless, for preparing same, in addition to the corresponding associated synthesis step, it must also be taken into account that, depending on the yield of the organic synthesis, mixtures of products can be obtained due to the incorporation of one amino group or two amino groups at the different ends of the linear dihaloalkane, an additional purification step then being required.

Therefore, there is a need in the chemical industry to find simpler organic molecules, such as monocationic OSDAs for example, which are capable of directing the formation of structure Beta in nanocrystalline form with crystal sizes smaller than 50 nm, with wide ranges of chemical composition and good synthesis yields (>90%).

Despite the breakthroughs shown in the synthesis of structure Beta in nanocrystalline form, there is a clear need in the chemical industry to improve its synthesis for subsequently applying same in various catalytic processes, and more particularly for use as a catalyst in processes of aromatic alkylation, or in processes for the oligomerisation of light olefins for producing synthetic liquid fuels.

DESCRIPTION OF THE INVENTION

The present invention relates to a new synthesis method for synthesising zeolite with structure Beta in nanocrystalline form, using a monocationic OSDA to obtain high synthesis yields (>80%) and an average crystal size smaller than 50 nm. The present invention also relates to the subsequent use of said synthesised material as a catalyst in various catalytic processes, preferably as a catalyst in processes for aromatic alkylation and oligomerisation of olefins.

In a first aspect, the present invention relates to a new synthesis method for synthesising a zeolite material with structure Beta in nanocrystalline form, which can comprise at least the following steps:

i) preparing a mixture comprising at least one source of water, at least one source of a tetravalent element Y, at least one source of a trivalent element X, at least one source of an alkali cation or alkaline earth metal cation (A), and at least one organic molecule (OSDA1), wherein OSDA1 can be selected from a monocyclic quaternary ammonium with the structure $R_1R_2CycloN^+$, where the Cyclo group may comprise 4-7 carbon atoms, and groups $R_1$ and $R_2$ can be linear alkyl chains comprised of 1-4 and 3-6 carbon atoms, respectively; and a quaternary ammonium substituted with a cycloalkyl group with structure $R_3R_4R_5R_6N^+$, wherein $R_3$ and $R_4$ can be linear alkyl chains comprised of 1-4 carbon atoms, $R_5$ can be a linear alkyl chain comprised of 4-6 carbon atoms, and $R_6$ is a cycloalkyl group which can be formed form 5-8 carbon atoms. The molar composition of the mixture is:

$nX_2O_3:YO_2:aA:mOSDA1:zH_2O$ wherein n is comprised in the range of 0 to 0.5, preferably 0.003 to 0.1; and more preferably 0.005 to 0.05;

a is comprised in the range of 0 to 2, preferably 0 to 1; and more preferably 0 to 0.8;

m is comprised in the range of 0.01 to 2, preferably 0.1 to 1; and more preferably 0.1 to 0.6; and z is comprised in the range of 1 to 200, preferably 1 to 50, and more preferably 2 to 20;

ii) crystallising the mixture obtained in i) in a reactor; and iii) recovering the crystalline material obtained in ii).

In the present invention, the term "Cyclo" refers to a linear alkyl chain of 4-7 carbon atoms, optionally substituted with an alkyl of 1 to 3 carbon atoms, preferably a methyl, the terminal carbons of which bind to N of the corresponding quaternary ammonium, such that said linear alkyl chain together with the N atom form a heterocycle.

According to a particular embodiment, the tetravalent element Y can be selected from silicon, tin, titanium, zirconium, germanium, and combinations thereof. Preferably, the source of element Y is a source of silicon which can be selected from, silicon oxide, silicon halide, colloidal silica, fumed silica, tetraalkyl orthosilicate, silicate, silicic acid, a previously synthesised crystalline material, a previously synthesised amorphous material, and combinations thereof.

According to a particular embodiment, the source of silicon can be selected from a previously synthesised crystalline material, a previously synthesised amorphous material, and combinations thereof, and optionally further contains other heteroatoms in its structure. Some examples could be faujasite type (FAU) zeolites, type L (LTL) and ordered amorphous mesoporous materials, such as MCM-41. These previously synthesised materials may further contain other heteroatoms in their structure, such as aluminium, for example.

According to a preferred embodiment, the trivalent element X can be selected from aluminium, boron, iron, indium, gallium, and combinations thereof; preferably aluminium, boron, and combinations thereof; and more preferably X is aluminium.

According to a particular embodiment, the trivalent element X is aluminium. Said source of aluminium can be selected from at least any aluminium salt (for example aluminium nitrate), or any hydrated aluminium oxide.

According to a particular embodiment of the present invention, the OSDA1 can be selected from alkyl-pyrrolidiniums, alkyl-piperidiniums, alkyl-hexamethyleneammoniums, alkyl-cyclopentylammoniums, alkyl-cyclohexylammoniums, alkyl-cycloheptylammoniums, and combinations thereof. Preferably said OSDA1 is N-butyl-N-methyl hexamethyleneammonium, N-butyl-N,N-dimethylcyclohexylammonium, or N-butyl-N,N-dimethylcycloheptylammonium.

According to the present invention, the crystallisation step described in ii) is preferably carried out in autoclaves, under static or dynamic conditions, at a temperature selected from between 80 and 200° C., preferably between 120 and 175° C., and more preferably between 130 and 175° C.; and a crystallisation time which can be comprised between 6 hours and 50 days, preferably between 1 and 14 days, and more preferably between 2 and 10 days. It must be taken into account that the components of the synthesis mixture can come from different sources, which may vary the described crystallisation conditions.

According to a particular embodiment of the method of the present invention, Beta crystals can be added to the synthesis mixture, acting as seeds favouring the described synthesis, in an amount of up to 25% by weight with respect to the total amount of the oxides corresponding to the sources of X and Y introduced in step i). These crystals can be added before or during the crystallisation process.

According to the described method, after the crystallisation described in ii), the resulting solid is separated from the mother liquor and recovered. The recovery step iii) can be carried out using different known separation techniques such as, for example, decantation, filtration, ultrafiltration, centrifugation, or any other solid-liquid separation technique and combinations thereof.

The method of the present invention may further comprise the removal of the organic content trapped within the material by means of any known removal/extraction technique.

According to a particular embodiment, the removal of the organic compound trapped within the material can be carried out by means of heat treatment at temperatures greater than 25° C., preferably between 100 and 1000° C. and for a time period preferably comprised between 2 minutes and 25 hours.

According to another particular embodiment, the material produced according to the present invention can be pelletised using any known technique.

According to a preferred embodiment, any cation present in the material can be exchanged by means of ion exchange with other cations using conventional techniques. Therefore, depending on the $X_2O_3/YO_2$ molar ratio of the synthesised material, any cation present in the material can be exchanged, at least in part, by means of ion exchange. Said cations can preferably be selected from metals, protons, proton precursors, and mixtures of same; and more preferably the exchange cation is a metal selected from rare-earth metals, metals from groups IIA, IIIA, IVA, VA, IB, IIB, IIIB, IVB, VB, VIB, VIIB, VIII, and combinations thereof.

Another aspect of the invention relates to a zeolite material with structure Beta obtained according to the method described above and characterised in that it has the following molar composition:

$$oX_2O_3:YO_2:pA:qOSDA1:rH_2O$$

wherein
X is a trivalent element;
Y is a tetravalent element;
A is an alkali cation or alkaline earth metal cation;
o is comprised in the range of 0 to 0.5, preferably 0.003 to 0.1; and more
preferably 0.005 to 0.05;
p is comprised in the range of 0 to 2, preferably 0 to 1; and more preferably 0 to 0.8;
q is comprised in the range of 0.01 to 2, preferably 0.1 to 1 and more preferably 0.1 to 0.6; and
r is comprised in the range of 0 to 2, preferably 0 to 1.5; and more preferably 0 to 1.

According to a preferred embodiment, the material obtained according to the present invention can be calcined. Thus, the zeolite material with structure Beta can have the following molar composition after being calcined:

$$oX_2O_3:YO_2:pA$$

wherein
X is a trivalent element;
Y is a tetravalent element;
A is an alkali cation or alkaline earth metal cation;
o is comprised in the range between 0 and 0.5, preferably 0.003 to 0.1; and more preferably 0.005 to 0.05; and
p is comprised in the range of 0 to 2, preferably 0 to 1; and more preferably 0 to 0.8.

As has been discussed, in the method described above, any cation present in the material can be exchanged by means of ion exchange with other cations using conventional techniques. Therefore, depending on the $X_2O_3/YO_2$ molar ratio of the synthesised material, any cation present in the material can be exchanged, at least in part, by means of ion exchange. These exchange cations are preferably selected from metals, protons, proton precursors (such as ammonium ions for example) and mixtures of same; more preferably said cation is a metal selected from rare-earth metals, metals from groups IIA, IIIA, IVA, VA, IB, IIB, IIIB, IVB, VB, VIB, VIIB, VIII, and combinations thereof, and heat-treated after that.

The crystalline material of the present invention can also be intimately combined with hydrogenating-dehydrogenating components such as, for example, platinum, palladium, nickel, rhenium, cobalt, tungsten, molybdenum, vanadium, chromium, manganese, iron and combinations thereof. The introduction of these elements can be carried out in crystallisation step ii), by exchange (where appropriate), and/or impregnation or physical mixing. These elements can be introduced in cationic form and/or from salts or other compounds which generate the oxide or metallic component in suitable catalytic form by decomposition.

In the described zeolite material with structure Beta, the tetravalent element Y can be selected from silicon, tin, titanium, zirconium, germanium, and combinations thereof, preferably silicon, and the trivalent element X can be selected from aluminium, boron, iron, indium, gallium and combinations thereof, preferably aluminium and boron; and more preferably aluminium.

A third aspect of the invention relates to the use of the materials described above and obtained according to the synthesis method of the present invention as catalysts for the conversion of feeds formed by organic compounds into products with a higher added value, or as a molecular sieve for the removal/separation of reactive streams (for example mixtures of gases) by contacting the feeds with the obtained material.

According to a preferred embodiment, the material obtained according to the present invention can be used as a catalyst in aromatic alkylation processes, where the alkylatable aromatic compound can be selected from benzene, biphenyl, naphthalene, anthracene, phenanthrene, thiophene, benzothiophene, substituted derivatives of same and combinations thereof, and the alkylating agent is selected from olefins, alcohols, polyalkylated aromatic compounds and combinations thereof. The obtained material, which may or may not contain hydrogenating-dehydrogenating components, can be used in processes for the dealkylation of alkylaromatics, transalkylation of alkylaromatics, isomerisation of alkylaromatics, or in combined processes for the dealkylation and transalkylation of alkylaromatics.

According to a preferred embodiment, the material obtained according to the present invention can be used as a catalyst in processes for oligomerisation of light olefins, such as, for example, propene, butene, or pentene, for the production of synthetic liquid fuels in the gasoline or diesel range.

Throughout the description and the claims, the word "comprises" and its variants do not intend to exclude other technical features, additives, components or steps. For those skilled in the art, other objects, advantages and features of the invention may be inferred from both the description and the embodiment of the invention.

Figure 1:
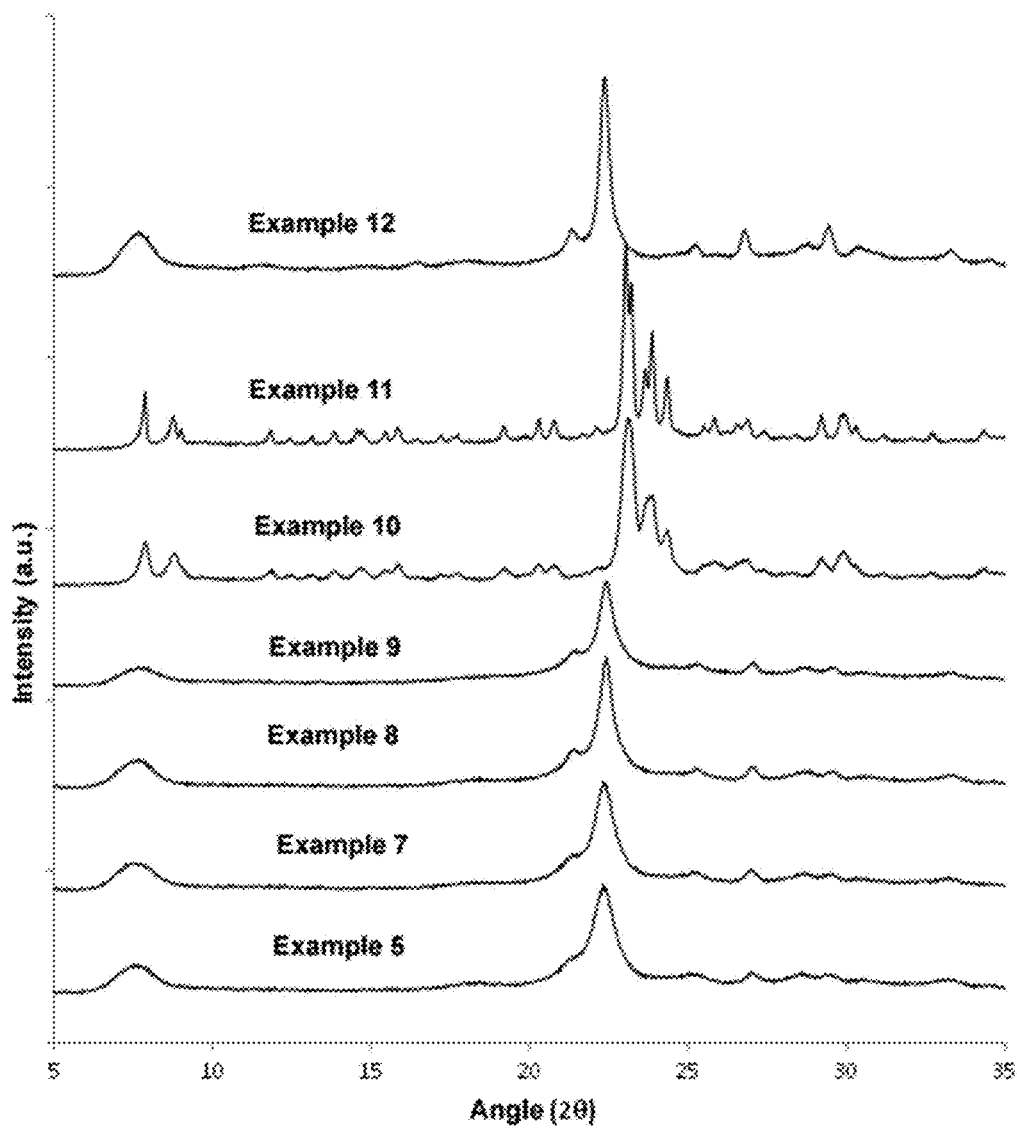
FIG. 1: Diffraction patterns of the materials obtained in Examples 5-12 of the present invention.

The present invention is illustrated by means of the following examples not intended to be limiting thereof.

EXAMPLES

The invention is illustrated below by means of tests conducted by the inventors that demonstrate the effectiveness of the product of the invention.

Example 1: Synthesis of N-butyl-N-methyl hexamethyleneammonium (BMH)

The reagent 1-bromobutane (60.88 g; 0.445 moles) is added dropwise to a solution of hexamethyleneimine (44.14 g; 0.444 moles) in anhydrous dimethylformamide (250 ml) under inert atmosphere, maintaining vigorous stirring. Next, the mixture is heated at 70° C. and left to react for 16 h. The mixture is left to cool and a crystalline white solid corresponding to the bromide salt of N-butylhexamethyleneammonium is formed, and separated by low pressure filtration. The crystals are washed to remove dimethylformamide residues and dried under low pressure and heat. Next, said salt (50.39 g; 0.213 moles) is dissolved in 400 ml of water, anhydrous $Na_2CO_3$ (22.61 g; 0.213 moles) is added and it is left to react at room temperature under strong stirring. As the reaction takes place, a two-phase mixture is formed. The resulting mixture is transferred to a decantation funnel. The phases are separated and the organic phase is set aside, and washed with a saturated NaCl solution (100 ml). Lastly, said phase is dried with anhydrous MgSO$_4$ and filtered to separate the inorganic salt. N-butylhexamethyleneimine is obtained as a colourless dense liquid.

Next, N-butylhexamethyleneimine (21.84 g; 0.141 moles) is dissolved in 200 ml of chloroform and the solution is cooled in an ice bath. Once the solution reaches 0° C., iodomethane (39.91 g; 0.281 moles) is added dropwise. When the system reaches room temperature, it is left to react for 72 h. Once the reaction has ended, the solvent is evaporated and a large volume of ethyl acetate is added to precipitate the compound. N-butyl-N-methyl hexamethyleneammonium iodide is obtained as a white solid.

To prepare the hydroxide form of the preceding organic salt: 15 g of the organic salt are dissolved in 75 g of water. Next 38 g of an anionic exchange resin (Dower SBR) are added, and the resulting mixture is kept under stirring for 24 hours. Lastly, the solution is filtered and N-butyl-N-methyl hexamethyleneammonium hydroxide is obtained.

Example 2: Synthesis of
N-butyl-N,N-dimethylcyclohexylammonium
(BDMC6)

8.18 g (0.064 moles) of N,N-dimethylcyclohexylamine are dissolved in 100 ml of acetonitrile. Five equivalents of 1-bromobutane (44.05 g, 0.321 moles) are added and left to react for 48 hours under vigorous stirring at reflux temperature (about 90° C. for acetonitrile). Once the reaction has ended the solvent is evaporated, obtaining a white crystalline residue. The solid is dissolved in a small aliquot of chloroform and a mixture of ethyl acetate-diethyl ether is added to crystallise the product. The compound is separated by filtration and finally dried by vacuum and heat.

To prepare the hydroxide form of the preceding organic salt: 15 g of the organic salt are dissolved in 75 g of water. Next 40 g of an anionic exchange resin (Dower SBR) are added, and the resulting mixture is kept under stirring for 24 hours. Lastly, the solution is filtered and N-butyl-N,N-dimethylcyclohexylammonium hydroxide is obtained.

Example 3: Synthesis of
N-butyl-N,N-dimethylcycloheptanammonium
(BDMC7)

11.8 g (0.104 moles) of cycloheptylamine are added to two-necked flask, provided with stirring and connected to a coolant. The flask is cooled in an ice bath (0° C.), and 6 equivalents of formaldehyde (18.79 g, 0.626 moles), and subsequently 6 equivalents of formic acid (28.80 g, 0.626 moles) are added under constant stirring. When the resulting mixture is stabilised and at room temperature, it is heated at 80° C. and left to react for about 15 hours. Once the reaction has ended, the mixture is cooled and an 8M NaOH solution is slowly added until reaching pH=13. The mixture is transferred to a decantation funnel and three extractions are performed with chloroform (30 ml). The organic phase is set aside and dried with anhydrous MgSO$_4$. After that it is filtered to separate the inorganic salts. Lastly, the solvent is evaporated and N,N-dimethylcycloheptylamine is obtained as a light yellow viscous liquid.

Next, 14.36 g of N,N-dimethylcycloheptylamine (0.102 moles) are dissolved in 200 ml of acetonitrile. Five equivalents of 1-bromobutane (41.82 g, 0.305 moles) are added and the solution is left to react at reflux temperature for 16 hours. The solvent is evaporated and the obtained residue is dissolved in a small volume of chloroform. N-butyl-N,N-dimethylcycloheptanammonium bromide is obtained by crystallisation by means of adding an ethyl acetate-hexane solution.

To prepare the hydroxide form of the preceding organic salt: 15 g of the organic salt are dissolved in 75 g of water. Next 38 g of an anionic exchange resin (Dower SBR) are added, and the resulting mixture is kept under stirring for 24 hours. Lastly, the solution is filtered and N-butyl-N,N-dimethylcycloheptylammonium hydroxide is obtained (with an exchange percentage of 96%).

Example 4: Synthesis of Triethylbutylammonium
(TEBA)

20.24 g (0.20 moles) of ethylisobutylamine are dissolved in 200 ml of chloroform. The mixture is cooled in an ice bath. Anhydrous K$_2$CO$_3$ (13.82 g; 0.10 moles) is added and left to react under constant stirring. Iodoethane (93.58 g; 0.60 moles) is slowly added by means of a pressure compensated funnel. After that it is heated at 50° C. and left to react for 24 hours. The mixture is cooled at room temperature, a new iodoethane aliquot (31 g, 0.20 moles) is added and it is left to react another 48 hours. After the reaction time has lapsed, the solvent is evaporated and the obtained residue is dissolved in dichloromethane. The crude product is filtered to separate the inorganic salts, setting aside the supernatant. Lastly, the solvent is evaporated and the product is crystallised by adding ethyl acetate.

To prepare the hydroxide form of the preceding organic salt: 15 g of the organic salt are dissolved in 75 g of water. Next 38 g of an anionic exchange resin (Dower SBR) are added, and the resulting mixture is kept under stirring for 24 hours. Lastly, the solution is filtered and triethylbutylammonium hydroxide is obtained.

Example 5: Synthesis of Nanocrystalline Beta in
Silicoaluminate Form 6.79 g of an aqueous solution at 7.61% by weight of BMH hydroxide (obtained according to Example 1 of the present invention) are mixed with 0.038 g of alumina [Al(OH)$_3$, Sigma-Aldrich]. The mixture is kept under stirring for 20 minutes. Next, 1.057 g of an aqueous solution of colloidal silica at 40% by weight (Ludox HS-40, Sigma-Aldrich) are added, and the mixture is kept under stirring until achieving the desired concentration. The final composition of the gel is SiO$_2$/0.0333 Al$_2$O$_3$/0.4 BMH/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is greater than 90%.

Figure 3:
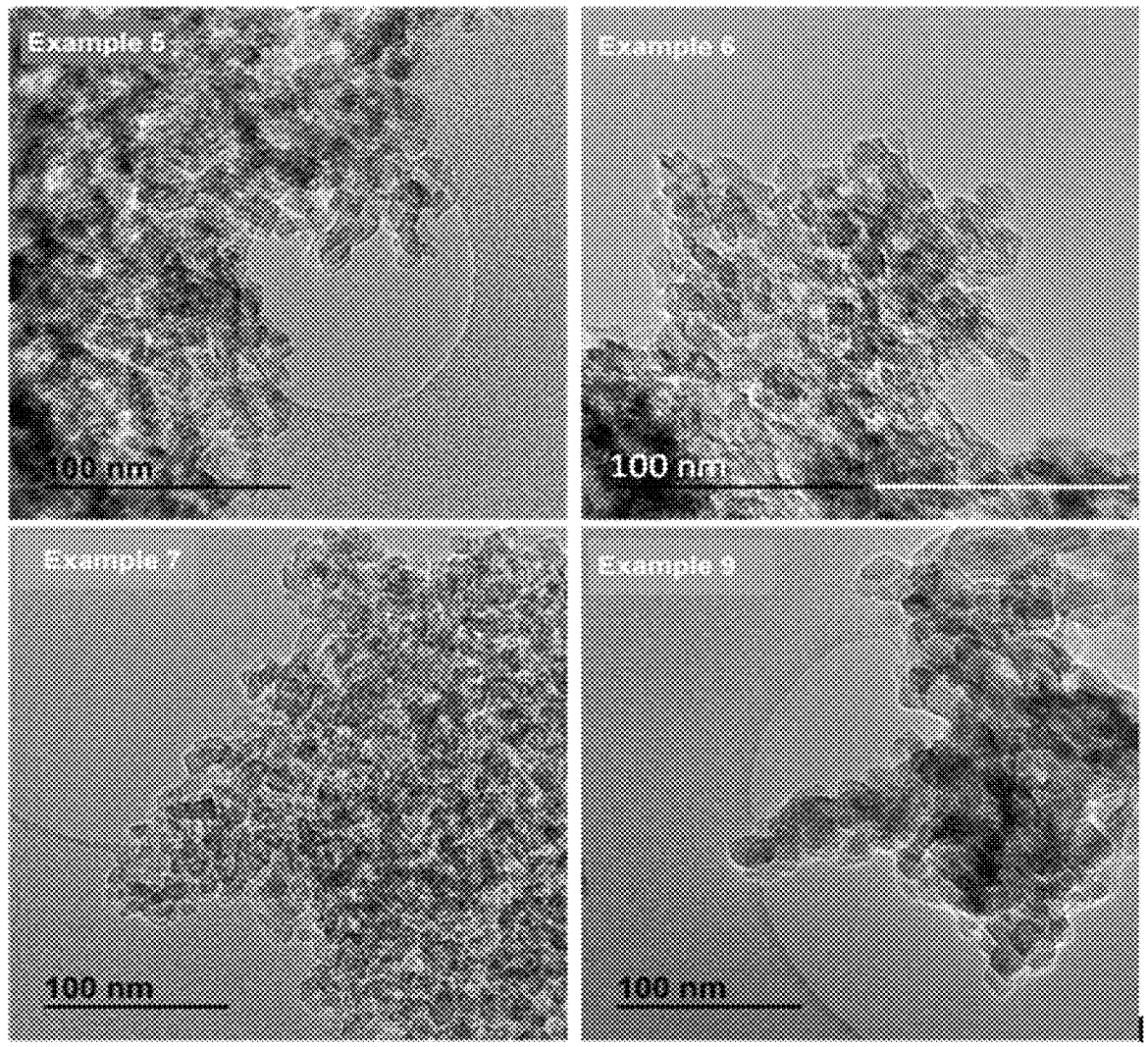
FIG. 3: TEM images of the materials obtained according to Examples 5, 6, 7 and 9 of the present invention.

It is confirmed by X-ray diffraction that the obtained solid has the characteristic peaks of Beta zeolite (see Example 5 in FIG. 1). The chemical composition of the final sample has a Si/Al ratio of 15.6. The average crystal size is ~10-15 nm (see TEM image in FIG. 3). The textural properties of the synthesised material according to Example 5 of the present invention have been calculated by N$_2$ adsorption/desorption, obtaining 733 m$^2$/g, 399 m$^2$/g, and 334 m$^2$/g, for the total BET area, micropore area and external area, respectively. The high values of the BET area and external area are due to the small size of the Beta nanocrystals obtained according to the present example.

Example 6: Synthesis of Nanocrystalline Beta in Silicoaluminate Form 4.53 g of an aqueous solution at 7.61% by weight of BMH hydroxide (obtained according to Example 1 of the present invention) are mixed with 0.013 g of alumina [Al(OH)$_3$, Sigma-Aldrich]. The mixture is kept under stirring for 20 minutes. Next, 0.698 g of an aqueous solution of colloidal silica at 40% by weight (Ludox HS-40, Sigma-Aldrich) are added. As seed, 0.014 mg of the solid obtained according to Example 5 of the present invention (5% by weight with respect to % SiO$_2$ in the mixture) are added. The mixture is kept under stirring until achieving the desired concentration. The final composition of the gel is SiO$_2$/0.0167 Al$_2$O$_3$/0.4 BMH/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is greater than 95%.

It is confirmed by X-ray diffraction that the obtained solid has the characteristic peaks of Beta zeolite. The chemical composition of the final sample has a Si/Al ratio of 29.9. The average crystal size is ~10-15 nm (see TEM image in FIG. 3). The textural properties of the synthesised material according to Example 6 of the present invention have been calculated by N$_2$ adsorption/desorption, obtaining 682 m$^2$/g, 429 m$^2$/g, and 252 m$^2$/g, for the total BET area, micropore area and external area, respectively. The high values of the BET area and external area are due to the small size of the Beta nanocrystals obtained according to the present example.

Example 7: Synthesis of Nanocrystalline Beta in Silicoaluminate Form 36.66 g of an aqueous solution at 7.91% by weight of BDMC6 hydroxide (obtained according to Example 2 of the present invention) are mixed with 0.196 g of alumina [Al(OH)$_3$, Sigma-Aldrich]. The mixture is kept under stirring for 20 minutes. Next, 5.401 g of an aqueous solution of colloidal silica at 40% by weight (Ludox HS-40, Sigma-Aldrich) are added, and the mixture is kept under stirring until achieving the desired concentration. The final composition of the gel is SiO$_2$/0.0333 Al$_2$O$_3$/0.4 BDMC6/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is greater than 95%.

Figure 2:
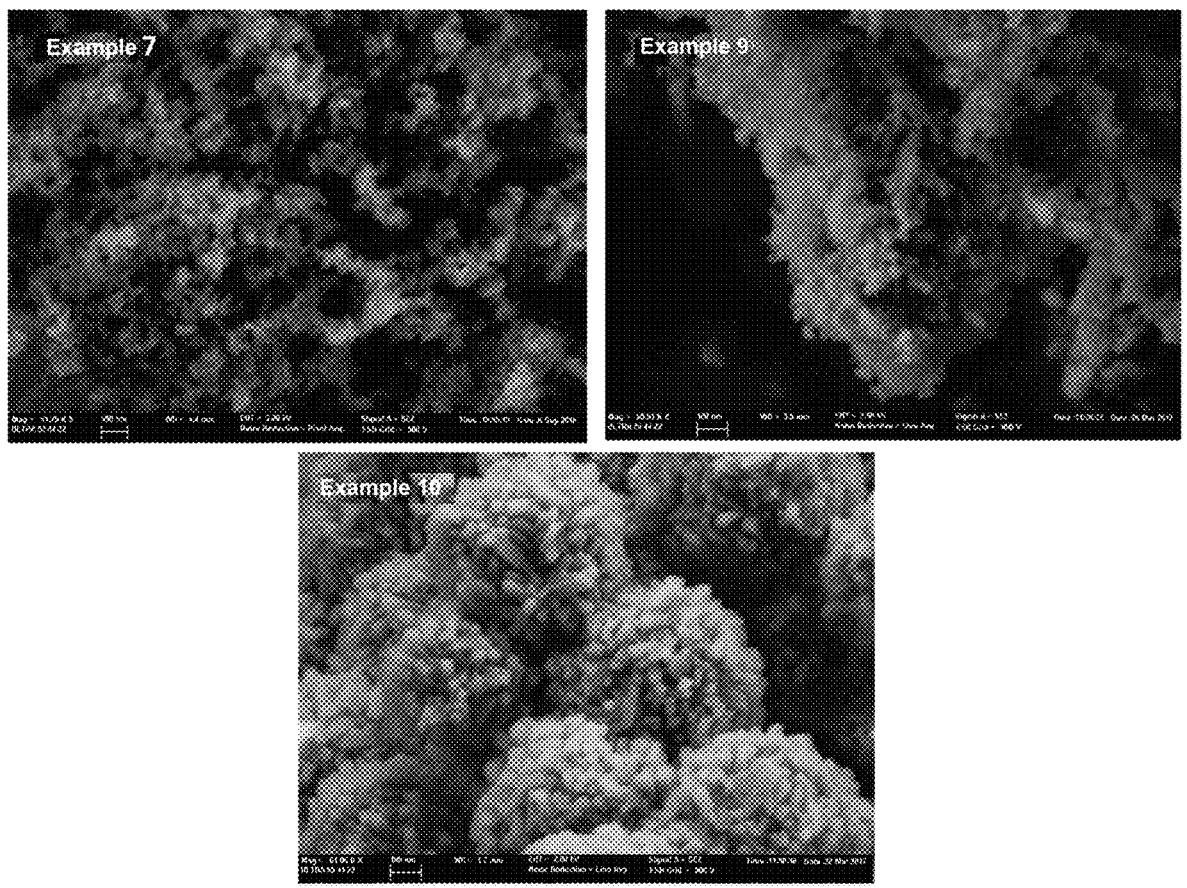
FIG. 2: SEM images of the materials obtained according to Examples 7, 9 and 10 of the present invention.

It is confirmed by X-ray diffraction that the obtained solid has the characteristic peaks of Beta zeolite (see Example 7 in FIG. 1). The chemical composition of the final sample has a Si/Al ratio of 15.6. The average crystal size is ~10-15 nm (see SEM and TEM images in FIGS. 2 and 3).

Example 8: Synthesis of Nanocrystalline Beta in Silicoaluminate Form 2.258 g of an aqueous solution at 5.71% by weight of BDMC6 hydroxide (obtained according to Example 2 of the present invention) are mixed with 0.005 g of alumina [Al(OH)$_3$, Sigma-Aldrich]. The mixture is kept under stirring for 20 minutes. Next, 0.249 g of an aqueous solution of colloidal silica at 40% by weight (Ludox HS-40, Sigma-Aldrich) are added, and the mixture is kept under stirring until achieving the desired concentration. The final composition of the gel is SiO$_2$/0.0167 Al$_2$O$_3$/0.4 BDMC6/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is greater than 90%.

It is confirmed by X-ray diffraction that the obtained solid has the characteristic peaks of Beta zeolite (see Example 8 in FIG. 1). The chemical composition of the final sample has a Si/Al ratio of 25.2.

Example 9: Synthesis of Nanocrystalline Beta in Silicoaluminate Form 1.73 g of an aqueous solution at 12.4% by weight of BDMC7 hydroxide (obtained according to Example 3 of the present invention) are mixed with 0.013 g of alumina [Al(OH)$_3$, Sigma-Aldrich]. The mixture is kept under stirring for 20 minutes. Next, 0.372 g of an aqueous solution of colloidal silica at 40% by weight (Ludox HS-40, Sigma-Aldrich) are added, and the mixture is kept under stirring until achieving the desired concentration. The final composition of the gel is SiO$_2$/0.0333 Al$_2$O$_3$/0.4 BDMC7/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is close to 100%.

It is confirmed by X-ray diffraction that the obtained solid has the characteristic peaks of Beta zeolite (see Example 9 in FIG. 1). The chemical composition of the final sample has a Si/Al ratio of 16.9. The average crystal size is ~10-15 nm (see SEM and TEM images in FIGS. 2 and 3).

Example 10: Synthesis Using Triethylbutylammonium (TEBA) as OSDA 1.25 g of an aqueous solution at 8.03% by weight of TEBA hydroxide (obtained according to Example 4 of the present invention) are mixed with 0.012 g of alumina [Al(OH)$_3$, Sigma-Aldrich]. Next, 0.070 g of an aqueous solution at 20% by weight of sodium hydroxide (NaOH, Sigma-Aldrich, 98%) are added. The mixture is kept under stirring for complete homogenisation for 20 minutes. 0.358 g of an aqueous solution of colloidal silica at 40% by weight (Ludox HS-40 colloidal silica, Sigma-Aldrich) are added to the mixture, and the mixture is kept under stirring until achieving the desired concentration. The final composition of the gel is SiO$_2$/0.0333 Al$_2$O$_3$/0.15 NaOH/0.25 TEBA/10H$_2$O. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours.

It is confirmed by X-ray diffraction that the obtained solid has the characteristic peaks of structure MFI (see Example 10 in FIG. 1). The chemical composition of the final sample has a Si/Al ratio of 20.0. The average crystal size is ~100 nm (see SEM image in FIG. 2). This example shows that the absence of a cyclic group in the OSDA, together with the combination of linear alkyl groups of different sizes (in this case, a butyl and three ethyls), results in crystallising a phase other than Beta, in particular MFI, and furthermore the average size of the crystals is significantly larger.

Example 11: Synthesis Using Triethylbutylammonium (TEBA) as OSDA 2.01 g of an aqueous solution at 8.0% by weight of TEBA hydroxide (obtained according to Example 4 of the present invention) are mixed with 0.006 g of alumina [Al(OH)$_3$, Sigma-Aldrich]. The mixture is kept under stirring for complete homogenisation for 20 minutes. 0.349 g of an aqueous solution of colloidal silica at 40% by weight (Ludox HS-40 colloidal silica, Sigma-Aldrich) are added to the mixture, and the mixture is kept under stirring until achieving the desired concentration. The final composition of the gel is $SiO_2/0.0167$ $Al_2O_3/0.4$ TEBA/$10H_2O$. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours.

It is confirmed by X-ray diffraction that the obtained solid has the characteristic peaks of structure MFI (see Example 11 in FIG. 1). The chemical composition of the final sample has a Si/Al ratio of 32.4. The average crystal size is ~100 nm. This example shows that the absence of a cyclic group in the OSDA, together with the combination of linear alkyl groups of different sizes (in this case, a butyl and three ethyls), results in crystallising a phase other than Beta, in particular MFI, and furthermore, the average size of the crystals is significantly larger.

Example 12: Synthesis Using Tetraethylammonium (TEA) as OSDA 6.74 g of an aqueous solution at 35% by weight of the tetraethylammonium hydroxide (TEA) are mixed with 0.214 g of alumina [Al(OH)$_3$, Sigma-Aldrich]. The mixture is kept under stirring for 20 minutes. Next, 6.0 g of an aqueous solution of colloidal silica at 40% by weight (Ludox HS-40, Sigma-Aldrich) are added, and the mixture is kept under stirring until achieving the desired concentration. The final composition of the gel is $SiO_2/0.0333$ $Al_2O_3/0.4$ TEAOH/$10H_2O$. This gel is transferred to a Teflon-lined steel autoclave and heated at 150° C. for 14 days under static conditions. After this time has lapsed, the obtained product is recovered by filtration, washed with abundant water, and dried at 100° C. The obtained solid is calcined in air at 550° C. for 5 hours. The obtained solid yield is 50%, much smaller than the yields obtained in Examples 5-9 of the present invention using the monocyclic cations described in Examples 1-3 as OSDAs.

It is confirmed by X-ray diffraction that the obtained solid has the characteristic peaks of Beta zeolite (see Example 12 in FIG. 1). The chemical composition of the final sample has a Si/Al ratio of 15.6. The average crystal size is ~40-50 nm. The textural properties of the synthesised material according to Example 12 of the present invention have been calculated by $N_2$ adsorption/desorption, obtaining 530 m$^2$/g, 396 m$^2$/g, and 134 m$^2$/g, for the total BET area, micropore area and external area, respectively. This example shows that the use of TEA as OSDA results in crystallising the Beta zeolite with an average crystal size larger than those obtained in Examples 5-9 of the present invention using the monocyclic cations described in Examples 1-3 as OSDAs, as demonstrated by the obtained lower values of BET and external area (compare with Examples 5 and 6).

Example 13: Synthesis of Nanocrystalline Beta in Borosilicate Form 13.28 g of an aqueous solution at 9.1% by weight of BDMC6 hydroxide (obtained according to Example 2 of the present invention) are mixed with 1.224 g of an aqueous solution at 5% of boric acid [H$_3$BO$_3$, Sigma-Aldrich]. The mixture is kept under stirring for 20 minutes. Next, 2.25 g of an aqueous solution of colloidal silica at 40% by weight (Ludox HS-40, Sigma-Aldrich) are added, and the mixture is kept under stirring until achieving the desired concentration. The final composition of the gel is $SiO_2/0.033$ $B_2O_3/0.4$ BDMC6/$10H_2O$. This gel is transferred to a Teflon-lined steel autoclave and heated at 175° C. for 10 days under static conditions. After this time has lapsed, the obtained product is recovered by filtration, washed with abundant water, and dried at 100° C. The obtained solid is calcined in air at 550° C. for 5 hours. The obtained solid yield is greater than 85%.

It is confirmed by X-ray diffraction that the obtained solid has the characteristic peaks of Beta zeolite. The chemical composition of the final sample has a Si/B ratio of 15.3. The average crystal size is ~15-30 nm.

Example 14: Catalytic Assay for the Alkylation Reaction of Benzene with Propylene Using the Synthesised Material According to Example 7

The synthesised material according to Example 7 has been pelletised selecting the particle size between 0.25 and 0.42 mm to carry out the alkylation reaction of benzene with propylene. Beta zeolite (0.200 g) is diluted with silicon carbide (0.59-0.84 mm) to a total catalyst bed volume of 3.6 ml. The diluted catalyst is introduced in a tubular steel reactor with a diameter of 1 cm and is activated under nitrogen flow (100 ml/min) at 200° C. for 2 hours. Next, the temperature is lowered to the reaction temperature of 125° C. under $N_2$ flow. When achieved the target temperature, the $N_2$ flow is interrupted and a mixture of benzene:n-octane (ratio of 15:1 by weight) is fed in until achieving a pressure of 3.5 MPa, where the n-octane is used as an internal standard and is inert in the experimental conditions used. At this point the reactor is isolated to feed in a mixture of benzene:n-octane (655 μl/min) and propylene (165 μl/min), the benzene/propylene molar ratio being 3.5, through a parallel conduit until achieving a constant composition, at which time the feed is passed through the reactor again, and it is considered the start of the reaction. Under these experimental conditions, the space velocity, WHSV (Weight Hour Space Velocity) in reference to propylene, is 25 h$^{-1}$, and the benzene is in liquid phase. The composition of the stream at the outlet of the reactor has been analysed by gas chromatography in a Varian 450 connected in line, equipped with a 5% phenyl-95% dimethylpolysiloxane capillary column and with a flame ionisation detector (FID).

The catalytic results obtained with the synthesised material according to Example 7 of the present invention are shown in Table 1.

TABLE 1

Conversion of propylene (X, %) and yield into
products (isopropylbenzene, $R_{IPB}$, diisopropylbenzene,
$R_{DIPB}$, and triisopropylbenzene, $R_{TIPB}$, % weight)
obtained in the alkylation reaction of benzene
with propylene, using as a catalyst the materials
prepared according to Example 7.

| Catalyst | Example 7 | | | |
|---|---|---|---|---|
| TOS (min) | X | $R_{IPB}$ | $R_{DIPB}$ | $R_{TIPB}$ |
| 25 | 97.7 | 78.1 | 15.2 | 4.2 |
| 52 | 85.0 | 70.6 | 11.2 | 2.4 |
| 106 | 72.4 | 58.8 | 8.7 | 0.9 |
| 214 | 52.3 | 45.1 | 5.8 | 0.6 |
| 300 | 39.3 | 36.1 | 3.0 | 0.2 |

Example 15: Catalytic Assay for the Alkylation Reaction of Benzene with Propylene Using the Synthesised Material According to Example 12

The synthesised material according to Example 12 has been pelletised selecting the particle size between 0.25 and 0.42 mm to carry out the alkylation reaction of benzene with propylene following the same method described in Example 14.

The catalytic results obtained with the synthesised material according to Example 12 of the present invention are shown in Table 2 (comparison with synthesised nanocrystalline Beta zeolite according to Example 7 of the present invention can be seen in Table 1).

TABLE 2

Conversion of propylene (X, %) and yield into products
(isopropylbenzene, $R_{IPB}$, diisopropylbenzene, $R_{DIPB}$, and
triisopropylbenzene, $R_{TIPB}$, % weight) obtained in
the alkylation reaction of benzene with propylene,
using as a catalyst the material prepared according
to Example 12 of the present invention.

| Catalyst | Example 12 | | | |
|---|---|---|---|---|
| TOS (min) | X | $R_{IPB}$ | $R_{DIPB}$ | $R_{TIPB}$ |
| 25 | 44.1 | 39.4 | 4.1 | <0.1 |
| 52 | 30.2 | 28.3 | 1.8 | <0.1 |
| 106 | 19.6 | 18.5 | 1.0 | <0.1 |
| 214 | 9.0 | 8.6 | 0.3 | <0.1 |
| 300 | 7.7 | 7.4 | 0.3 | <0.1 |

Example 16: Catalytic Assay for the Alkylation Reaction of Benzene with Propylene Using a Commercial Beta Zeolite Commercial Beta zeolite, CP811 (Zeolyst Int.) has been pelletised selecting the particle size between 0.25 and 0.42 mm to carry out the alkylation reaction of benzene with propylene following the same method described in Example 14.

The catalytic results obtained are shown in Table 3.

Upon comparison of the results of the three materials presented in Table 1, 2 and 3, it is concluded that the catalyst based on Beta zeolite obtained according to Example 7 is much more active than the catalyst based on Beta zeolite obtained according to Example 12 and more active than the catalyst based on commercial Beta zeolite CP811. Thus, the conversions of propylene at a reaction time (TOS, Time On Stream) of 25 min are 97.7, 44.1 and 64.2%, respectively. Furthermore, the catalyst based on the material obtained according to Example 7 produces a higher yield into the alkylation product, isopropylbenzene (IPB).

TABLE 3

Conversion of propylene (X, %) and yield into products
(isopropylbenzene, $R_{IPB}$, diisopropylbenzene, $R_{DIPB}$,
and triisopropylbenzene, $R_{TIPB}$, % weight) obtained in
the alkylation reaction of benzene with propylene, using
as a catalyst commercial Beta zeolite CP811.

| Catalyst | CP811 | | | |
|---|---|---|---|---|
| TOS (min) | X | $R_{IPB}$ | $R_{DIPB}$ | $R_{TIPB}$ |
| 25 | 64.2 | 59.9 | 4.2 | 0.1 |
| 52 | 47.1 | 43.8 | 3.1 | 0.1 |
| 106 | 29.9 | 28.8 | 1.8 | <0.1 |
| 214 | 20.7 | 19.9 | 0.7 | <0.1 |
| 300 | 17.9 | 15.3 | 0.5 | <0.1 |

Example 17: Catalytic Assay for the Oligomerisation Reaction of 1-Pentene Using the Synthesised Material According to Example 7

The synthesised material according to Example 7 has been pelletised selecting the particle size between 0.25 and 0.42 mm to carry out the oligomerisation reaction of 1-pentene. Beta zeolite (0.130 g) is diluted with silicon carbide (0.59-0.84 mm) to a total catalyst bed volume of 4.0 ml. The diluted catalyst is introduced in a tubular steel reactor with an internal diameter of 1 cm, and is activated by increasing to a temperature of 520° C. under nitrogen flow (200 ml/min), and being maintained at this temperature under an airflow (200 ml/min) for 5 hours. Next the temperature is lowered to the reaction temperature, 200° C., and the system is pressurised with $N_2$ until reaching the working pressure of 40 bar. At that time the reactor is isolated and the reactant mixture (1-pentene:n-heptane, in a molar ratio 60:40) is fed in through a parallel conduit until achieving a constant composition, at which time the feed is passed through the reactor again, and it is considered the start of the reaction. The space velocity, WHSV (Weight Hour Space Velocity) in reference to 1-pentene, has been varied in the range of 14.3 to 25 $h^{-1}$. Under these experimental conditions, the mixture is in liquid phase.

At the outlet of the reactor, the product stream is depressurised and vaporised to be analysed in line in a Varian 3400 gas chromatograph, equipped with a 60 m TRB-5 column, a flame ionisation detector (FID), and using n-heptane, which was inert under these experimental conditions, as an internal standard.

Furthermore, the mixture of products $C_5$, is condensed and analysed by simulated distillation (excluding n-heptane from the naphtha fraction, for the determination of the selectiveness in liquids. The cut-off points for the considered fractions are the following:

Naphtha: C5-173.9° C.

Diesel: 173.9-391.1° C.

Heavy fraction: 391.1-1000° C.

The catalytic results of the synthesised material according to Example 7 of the present invention are summarized in Table 4.

TABLE 4

Conversion of 1-pentene (X, %) and yield into the different fractions of products in $C_{5+}$ (naphtha, $R_{NAPHTHA}$, diesel, $R_{DIESEL}$, and heavy, $R_{HEAVY}$, % weight) obtained in the oligomerisation reaction of 1-pentene, using as a catalyst the material prepared according to Example 7 of the present invention.

| Catalyst | Example 7 | | | |
|---|---|---|---|---|
| TOS (h) | X | $R_{NAPHTHA}$ | $R_{DIESEL}$ | $R_{HEAVY}$ |
| | WHSV = 14.3 $h^{-1}$ | | | |
| 0-3 | 89.6 | 34.5 | 62.2 | 3.3 |
| 3-6 | 83.7 | 43.3 | 54.3 | 2.4 |
| | WHSV = 25 $h^{-1}$ | | | |
| 0-3 | 89.7 | 50.0 | 47.9 | 2.1 |
| 3-6 | 77.3 | 58.9 | 39.6 | 1.5 |

Example 18: Catalytic Assay for the Oligomerisation Reaction of 1-Pentene Using the Synthesised Material According to Example 12

The synthesised material according to Example 12 has been pelletised selecting the particle size between 0.25 and 0.42 mm to carry out the oligomerisation reaction of 1-pentene following the same method described in Example 17.

The catalytic results obtained with the synthesised material according to Example 12 of the present invention are shown in Table 5.

TABLE 5

Conversion of 1-pentene (X, %) and yield into the different fractions of products in $C_{5+}$ (naphtha, $R_{NAPHTHA}$, diesel, $R_{DIESEL}$, and heavy, $R_{HEAVY}$, % weight) obtained in the oligomerisation reaction of 1-pentene, using as a catalyst the material prepared according to Example 12 of the present invention.

| Catalyst | Example 12 | | | |
|---|---|---|---|---|
| TOS (h) | X | $R_{NAPHTHA}$ | $R_{DIESEL}$ | $R_{HEAVY}$ |
| | WHSV = 14.3 $h^{-1}$ | | | |
| 0-3 | 73.4 | 63.8 | 34.8 | 1.4 |
| 3-6 | 60.8 | 67.4 | 31.7 | 0.9 |
| | WHSV = 25 $h^{-1}$ | | | |
| 0-3 | 65.6 | 73.9 | 25.4 | 0.7 |
| 3-6 | 39.3 | 80.5 | 18.6 | 0.9 |

Example 19: Catalytic Assay for the Oligomerisation Reaction of 1-Pentene Using a Commercial Beta Zeolite Commercial Beta zeolite, CP811 (Zeolyst Int.) has been pelletised selecting the particle size between 0.25 and 0.42 mm to carry out the oligomerisation reaction of 1-pentene following the same method described in Example 17.

The catalytic results obtained are shown in Table 6.

TABLE 6

Conversion of 1-pentene (X, %) and yield into the different fractions of products in $C_{5+}$ (naphtha, $R_{NAPHTHA}$, diesel, $R_{DIESEL}$, and heavy, $R_{HEAVY}$, % weight) obtained in the oligomerisation reaction of 1-pentene, using as a catalyst commercial Beta zeolite CP811.

| Catalyst | CP811 | | | |
|---|---|---|---|---|
| TOS (h) | X | $R_{NAPHTHA}$ | $R_{DIESEL}$ | $R_{HEAVY}$ |
| | WHSV = 14.3 $h^{-1}$ | | | |
| 0-3 | 73.6 | 54.1 | 45.6 | 0.3 |
| 3-6 | 40.7 | 59.4 | 40.4 | 0.2 |
| | WHSV = 25 $h^{-1}$ | | | |
| 0-3 | 51.2 | 46.3 | 53.4 | 0.3 |
| 3-6 | 20.5 | 71.5 | 28.4 | 0.1 |

Upon comparison of the results of the three materials presented in Tables 4, 5 and 6, it is concluded that the catalyst based on Beta zeolite obtained according to Example 7 is much more active than the catalyst based on Beta zeolite obtained according to Example 12 and the catalyst based on commercial Beta zeolite CP811 for the oligomerisation of 1-pentene. Thus, the mean conversion of olefin at a space velocity, WHSV, of 25 $h^{-1}$, in the reaction time interval (TOS) of 0-3 hours, is 89.7, 65.6 and 51.2%, respectively.

The invention claimed is:

1. A synthesis method for synthesising a zeolite material with structure Beta in nanocrystalline form, characterised in that it comprises at least the following steps:
    i) preparing a mixture comprising at least one source of water, at least one source of a tetravalent element Y, at least one source of a trivalent element X, at least one source of an alkali cation or alkaline earth metal cation (A), and at least one organic molecule (OSDA1), wherein OSDA1 is selected from a quaternary ammonium of structure $R_1R_2CycloN^+$, wherein the Cyclo group comprises 4-7 carbon atoms, $R_1$ is a linear alkyl chain of 1 to 4 carbon atoms, and $R_2$ is a linear alkyl chain of 3 to 6 carbon atoms; and a quaternary ammonium of structure $R_3R_4R_5R_6N^+$, wherein $R_3$ and $R_4$ are, independently of one another, linear alkyl chains of 1 to 4 carbon atoms, $R_5$ is a linear alkyl chain of 4 to 6 carbon atoms, and $R_6$ is a cycloalkyl group of 5 to 8 carbon atoms, the molar composition of the mixture being:

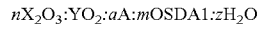
    $nX_2O_3:YO_2:aA:mOSDA1:zH_2O$ wherein
    n is comprised in the range of 0 to 0.5;
    a is comprised in the range of 0 to 2,
    m is comprised in the range of 0.01 to 2; and
    z is comprised in the range of 1 to 200;
    ii) crystallising the mixture obtained in i) in a reactor; and
    iii) recovering the crystalline material obtained in ii).

2. The method according to claim 1, characterised in that the tetravalent element Y is selected from silicon, tin, titanium, zirconium, germanium, and combinations thereof.

3. The method according to claim 2, characterised in that the source of the tetravalent element Y is a source of silicon which is selected from silicon oxide, silicon halide, colloidal silica, fumed silica, tetraalkyl orthosilicate, silicate, silicic acid, a previously synthesised crystalline material, a previously synthesised amorphous material, and combinations thereof.

4. The method according to claim 3, characterised in that the source of silicon is selected from a previously synthesised crystalline material, a previously synthesised amorphous material, and combinations thereof.

5. The method according to claim 4, characterised in that the previously synthesised materials contain other heteroatoms in their structure.

6. The method according to claim 1, characterised in that the trivalent element X is selected from aluminium, boron, iron, indium, gallium, and combinations thereof.

7. The method according to claim 1, characterised in that the OSDA1 is selected from alkyl-pyrrolidiniums, alkyl-piperidiniums, alkyl-hexamethyleneammoniums, alkyl-cyclopentylammoniums, alkyl-cyclohexylammoniums, alkyl-cycloheptylammoniums, and combinations thereof.

8. The method according to claim 7, characterised in that said OSDA1 is N-butyl-N-methyl hexamethyleneammonium, N-butyl-N,N-dimethylcyclohexylammonium, or N-butyl-N,N-dimethylcycloheptylammonium.

9. The method according to claim 1, characterised in that the crystallisation step described in ii) is carried out in autoclaves, under static or dynamic conditions.

10. The method according to claim 1, characterised in that the crystallisation process described in ii) is carried out at a temperature of between 80 and 200° C.

11. The method according to claim 1, characterised in that the crystallisation time of step ii) is comprised between 6 hours and 50 days.

12. The method according to claim 1, characterised in that it further comprises adding Beta zeolite crystals to the synthesis mixture in an amount of up to 25% by weight with respect to the total amount of the sources of X and Y introduced in step i).

13. The method according to claim 12, characterised in that the Beta crystals are added before the crystallisation process of step ii) or during the crystallisation process of step ii).

14. The method according to claim 1, characterised in that the recovery step iii) is carried out by means of a separation technique selected from decantation, filtration, ultrafiltration, centrifugation and combinations thereof.

15. The method according to claim 1, characterised in that it further comprises the removal of the organic content trapped within the material.

16. The method according to claim 15, characterised in that the process of removing the organic content isolated within the material is performed by heat treatment at temperatures between 100 and 1000° C. for a time period comprised between 2 minutes and 25 hours.

17. The method according to claim 1, characterised in that the obtained material is pelletised.

18. The method according to claim 1, characterised in that any cation present in the material is exchanged by means of ion exchange with other cations.

19. The method according to claim 18, characterised in that the exchange cation is selected from metals, protons, proton precursors, and mixtures of same.

20. The method according to claim 19, characterised in that the exchange cation is a metal selected from rare-earth metals, metals from groups IIA, IIIA, IVA, VA, IB, IIB, IIIB, IVB, VB, VIB, VIIB, VIII, and combinations thereof.

21. A zeolite material with structure Beta described in claim 1, characterised in that it has the following molar composition $$oX_2O_3:YO_2:pA:qOSDA1:rH_2O$$

wherein
X is a trivalent element;
Y is a tetravalent element;
A is an alkali or alkaline earth element;
o is comprised in the range of 0 to 0.5;
p is comprised in the range of 0 to 2;
q is comprised in the range of 0.01 to 2; and
r is comprised in the range of 0 to 2.

22. The zeolite material with structure Beta according to claim 21, characterised in that it has the following molar composition after being calcined:

$$oX_2O_3:YO_2:pA$$

wherein
X is a trivalent element;
Y is a tetravalent element; and
A is an alkali or alkaline earth element;
o is comprised in the range between 0 and 0.5; and
p is comprised in the range of 0 to 2.

23. The zeolite material with structure Beta according to claim 21, characterised in that the tetravalent element Y is selected from silicon, tin, titanium, zirconium, germanium, and combinations thereof.

24. The zeolite material with structure Beta according to claim 21, characterised in that the trivalent element X is selected from aluminium, boron, iron, indium, gallium, and combinations thereof.

25. The catalyst as catalysts for the conversion of feeds formed by organic compounds into products with a higher added value comprising the zeolite material with structure Beta according to claim 21.

26. The molecular sieve for the removal or separation of reactive streams comprising the zeolite material with structure Beta according to claim 21.

* * * * *